(12) United States Patent
Naviaux

(10) Patent No.: US 7,195,523 B2
(45) Date of Patent: Mar. 27, 2007

(54) ELECTRICAL CONDUCTIVE PATH FOR A MEDICAL ELECTRONICS DEVICE

(75) Inventor: Jacques Naviaux, Rancho Palos Verdes, CA (US)

(73) Assignee: Bal Seal Engineering Co., Inc., Lake Forest, CA (US)

( * ) Notice: Subject to any disclaimer, the term of this patent is extended or adjusted under 35 U.S.C. 154(b) by 55 days.

(21) Appl. No.: 11/208,092

(22) Filed: Aug. 19, 2005

(65) Prior Publication Data

US 2006/0047322 A1 Mar. 2, 2006

Related U.S. Application Data

(60) Provisional application No. 60/605,275, filed on Aug. 26, 2004.

(51) Int. Cl.
*H01R 13/17* (2006.01)
(52) U.S. Cl. .................. 439/827; 607/37; 439/668
(58) Field of Classification Search ............... 439/668, 439/669, 827; 607/36, 37
See application file for complete search history.

(56) References Cited

U.S. PATENT DOCUMENTS

| | | | | |
|---|---|---|---|---|
| 4,384,752 A | * | 5/1983 | Gabriel | 439/38 |
| 4,469,104 A | * | 9/1984 | Peers-Trevarton | 607/27 |
| 4,934,366 A | * | 6/1990 | Truex et al. | 607/37 |
| 4,989,173 A | * | 1/1991 | Kaneda | 708/653 |
| 5,304,219 A | * | 4/1994 | Chernoff et al. | 607/122 |
| 5,413,508 A | * | 5/1995 | Obara | 439/729 |
| 5,441,499 A | * | 8/1995 | Fritzsch | 606/45 |
| 5,477,856 A | * | 12/1995 | Lundquist | 600/373 |
| 5,545,188 A | * | 8/1996 | Bradshaw et al. | 607/37 |
| 5,720,631 A | * | 2/1998 | Carson et al. | 439/668 |
| 5,730,628 A | * | 3/1998 | Hawkins | 439/843 |
| 5,746,737 A | * | 5/1998 | Saadat | 606/15 |
| 5,843,141 A | | 12/1998 | Bischoff et al. | |
| 5,989,077 A | | 11/1999 | Mast et al. | |
| 6,162,101 A | | 12/2000 | Fischer et al. | |
| 6,321,126 B1 | | 11/2001 | Kuzma | |
| 6,662,035 B2 | | 12/2003 | Sochor | |
| 6,725,096 B2 | | 4/2004 | Chinn et al. | |
| 6,755,694 B2 | * | 6/2004 | Ries et al. | 439/668 |
| 6,816,745 B1 | * | 11/2004 | Brand et al. | 607/37 |
| 6,878,013 B1 | * | 4/2005 | Behan | 439/668 |
| 6,895,276 B2 | * | 5/2005 | Kast et al. | 607/37 |
| 7,058,452 B2 | * | 6/2006 | Dahlberg | 607/36 |
| 7,070,455 B2 | * | 7/2006 | Balsells | 439/668 |
| 7,083,474 B1 | * | 8/2006 | Fleck et al. | 439/668 |
| 7,110,827 B2 | * | 9/2006 | Sage et al. | 607/116 |
| 2002/0116035 A1 | * | 8/2002 | Klehn | 607/37 |
| 2003/0163171 A1 | | 8/2003 | Kast et al. | |
| 2004/0064164 A1 | * | 4/2004 | Ries et al. | 607/37 |

* cited by examiner

*Primary Examiner*—Briggitte Hammond
*Assistant Examiner*—Larisa Tsukerman
(74) *Attorney, Agent, or Firm*—Walter A. Hackler

(57) ABSTRACT

An electrical conductive path for medical electronic device generally includes a plurality of stackable molded non-conductive housing with each housing having a bore therethrough alignable with adjacent housing bores. The adjacent housings and define any combination when stacked, spaced apart slots for receiving a plurality of electrically conductive spring rings. A plurality of electrically conducting garter springs are disposed within corresponding spring rings and a cable is provided including wires attached to corresponding spring rings.

14 Claims, 2 Drawing Sheets

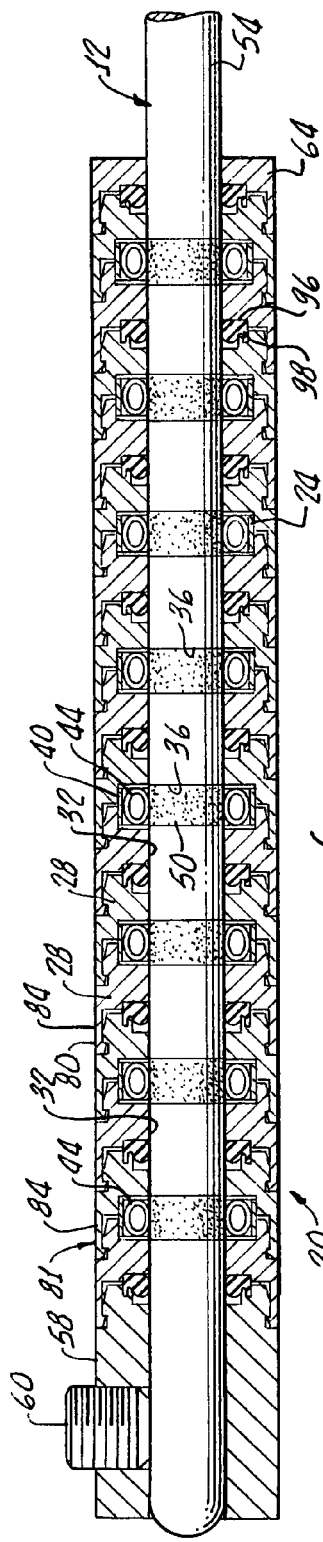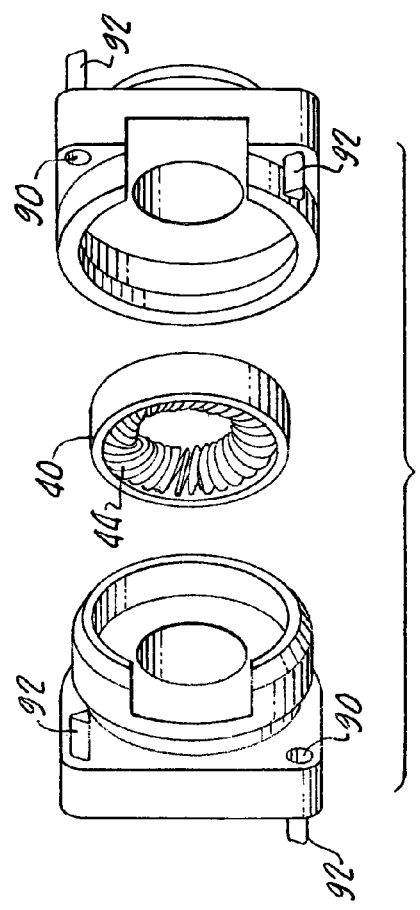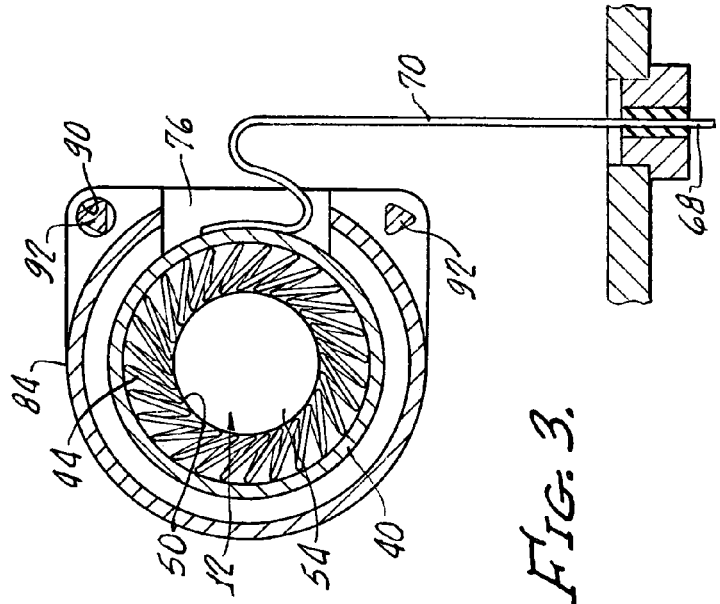

ent application claims priority from U.S. Ser. No. 60/605,275 filed Aug. 26, 2004 which is incorporated herewith in its entirety by this subject reference thereto.

ELECTRICAL CONDUCTIVE PATH FOR A MEDICAL ELECTRONICS DEVICE

The present application claims priority from U.S. Ser. No. 60/605,275 filed Aug. 26, 2004 which is incorporated herewith in its entirety by this subject reference thereto.

This invention is generally directed to implantable medical devices and is more particularly directed to the electrical conductive path between a pulse generator and the implantable lead or leads.

Implantable medical electronics devices consist of an implanted pulse generator that is used to provide electrical stimulation to certain tissues and an implantable lead or leads that are used to transmit the electrical impulse to the targeted tissues. The first ones were developed for cardiac pacemaking, and that area now has a number of applications for cardiac rhythm management, treatments for congestive heart failure, and implanted defibrillators. Other devices are used for neurostimulation with a wide range of uses such as pain control, nervous tremor mitigation, incontinent treatment, epilepsy seizure reduction, vagus nerve stimulation for clinical depression and others. This rapidly growing field will undoubtedly have even wider application in the future.

In general, the devices consist of an implanted pulse generator that may also be capable of sensing body activity such as an irregular heartbeat. The pulse generator generates an electrical pulse or signal that is transmitted to a targeted tissue or tissues or nerve area or areas through an implanted lead. Once the leads are implanted in the body, removal may involve major surgery with an attendant risk factor. Therefore, a reliable method of connecting and disconnecting the leads is required since the implanted pulse generator may have to be replaced to update the unit or to replace the battery.

The unit is a hermetically sealed enclosure containing the circuitry and a power supply. Current practice is to place a molded header containing a connector on top of the unit to provide a means of housing the electrical contacts for the leads. While some applications are very simple requiring only two leads because they only have to transmit two discrete signals to the tissues, others are very complex and require a very large number of discrete electrical impulses. Each electrical impulse then requires a discrete conductive path between the impulse generator and the implanted lead.

Several different types of contacts are in use ranging from setscrews to various types of spring contacts. These contacts are embedded in the connector which is generally made of a silicon filled implantable polymeric. The lead generally consists of a series of conductive rings separated by insulative spaces so that when it is fully inserted into the header, each contact ring is placed in contact with the connector contact. Each contact in turn has to be connected to a discrete lead from the pulse generator.

In current practice, the connector generally consists of a setscrew in a metal connector or some type of spring in a metal housing. Where the spring is used, it provides the conductive path between the metal housing and the contact ring of the lead. Setscrews are very undesirable where large numbers of connectors are required because each connector must be tightened with a torque wrench. A spring retained in a metal housing provides a reliable contact with controlled insertion forces that is convenient for both insertion and removal obviates the requirement for a torque wrench. A canted coil spring has very desirable characteristics for this application since its nearly constant force over a wide range of deflection compensates for any irregularities on the surface of the lead electrical contact rings and the insertion force can be controlled.

The housings, which can number anywhere from two to twenty-four or even more are now machined from metals such as MP35N, titanium, or even platinum, are significant cost drivers. The present invention utilizes an implantable polymeric biocompatible material housing that can be fabricated by injection molding to reduce the cost of the contacts with an electrical path.

SUMMARY OF THE INVENTION

The present invention provides for an electrical path through the use of a ring that is inserted into a molded housing for contacting a spring. Preferably, the housing is molded from an implantable polymeric material in two pieces with the ring, or spring ring, inserted between the two housings.

As hereinafter noted, various techniques may be utilized to secure the two halves of the housing to one another, while a preferable new embodiment enables the housing to snap together.

The spring ring may be cut to size from tubing and thus is dimensionally very accurate and consistent from ring to ring and it may be fabricated from any materials acceptable for implants.

In order to complete the electrical path from the pulse generator to a lead, the contact leads extending from the pulse generator are connected to the spring ring through windows provided for this purpose in the molded housing.

More particularly, an electrical conductive path for medical electronic device generally includes a plurality of stackable molded non-conductive housings with each housing having a bore therethrough alignable with adjacent housing bores with the adjacent housings defining, in combination, spaced apart slots.

A plurality of electrically conductive spring rings is disposed in corresponding slots and a plurality of electrically conducting garter springs are disposed within corresponding spring rings.

A cable is provided having a plurality of wire with each wire attached to a corresponding spring ring.

In one embodiment, snap fittings are provided for removably holding adjacent housings to one another. However, alternatively, the housings may include an alignable hole and pins for aligning the housing holes for assembling the housings adjacent to one another.

Still more particularly, the adjacent housings further define, in combination, seal grooves, and the path further comprises a plurality of washer seals with each washer seal being disposed in a corresponding seal groove.

As hereinabove noted, the housing may include windows for exposing the seal rings and wires communicating with a pulse generator are attached to corresponding spring rings within the windows.

More generally, the electrical conductive path for a medical electronic device may include a header along with a plurality of stackable molded non-conductive housings disposed in the header with each housing having a bore therethrough alignable with adjacent housing bores. The adjacent housings define, in combination, as hereinabove noted spaced apart slots.

In addition to the spring rings, garter springs and cable, hereinabove noted, the path may further include a lead including a rod receivable by the housing bores with each rod having a plurality of spaced apart electrical terminals corresponding to the spaced apart spring slots along with a latch for removably holding the rod in position within the bores with electrical connection between the corresponding rod terminals and springs.

BRIEF DESCRIPTION OF THE DRAWINGS

The present invention may be more clearly appreciated when taken in conjunction with the accompanying drawings, in which:

FIG. 2 shows the stackable connecting device that is located inside the header, generally including a plurality of contacts, (eight in this case), each contact being comprised of a molded plastic housing consisting of two halves joined together with a spring ring inside, and a canted coil spring inside the spring ring, a washer seal may be inserted between each contact to isolate the contact areas from any leakage, the setscrew and molded setscrew housing are also shown, a molded end cap, with the implantable lead are also shown;

FIG. 3 shows the spring ring exposed on a front of the connector to provide a welding surface; and FIG. 4 is an exploded view of the housing with a window to expose the spring ring along with a triangular pin and circular hole used to align the housing together upon assembly.

DETAILED DESCRIPTION

Figure 1:
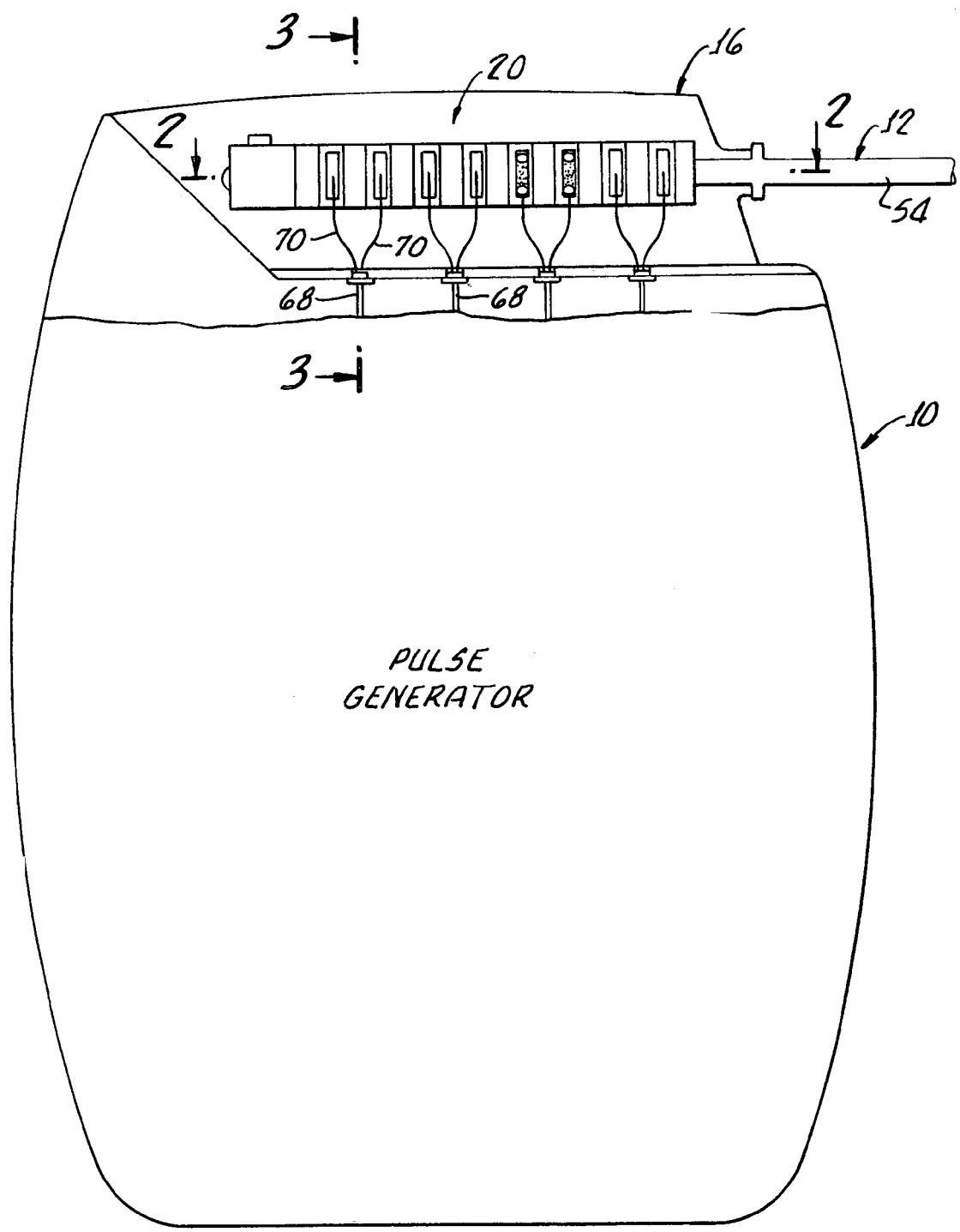
FIG. 1 shows a typical implantable medical electronics device consisting of a hermetically sealed pulse generator with a molded header connected to the generator containing a connecting device to connect the implantable lead or leads to the pulse generator, eight conductors being shown, however, the number of conductors may range from two to more than twenty-four, a setscrew may be used to retain the lead in the connector.

In general, FIG. 1 shows an implanted medical electronics device pulse generator 10. This device 10 generates electrical impulses that are delivered to target tissue (not shown) by a lead 12 that is also implanted. The pulse generator 10 may also be a receptor and processor of information from the targeted tissues through the implanted leads.

Devices 10 have a wide range of uses such as cardiac rhythm management, implanted defibrillators, neurostimulaters used for the control of pain, treatment of nervous disorders, incontinence, clinical depression and other applications.

The fundamental requirements are generally the same for most applications. An electrical signal must be transmitted from the pulse generator 10 to the implanted lead 12 to the targeted tissue. This invention is concerned with the transmission of the impulses signals from the pulse generator 10 to the lead 12.

A header 16 as shown in FIG. 1 is attached to the pulse generator 10. The header 16 contains the connecting device. The electrical signal is transmitted to the implantable lead 12 that is inserted into a connecting device 20 as shown in FIG. 2.

The lead 12 from the impulse generator 10 transmits the electrical impulse from the generator 10 to the implanted lead 12 though the connecting device 20. The connecting device 20 shown in FIG. 2 consists of a multiplicity of contacts 24. Each contact 24 has a discrete signal. The number of contacts 24 may vary from two to twenty four or higher. The electrical impulse travels from the pulse generator 10 to the contact 24.

More specifically, the device 20, path 24 in accordance with the present invention for the medical electronic device 10 includes a plurality of stackable molded non-conductive housings 28, see also FIGS. 3–4, with each housing 28 having a bore 32 therethrough which is alignable with adjacent housing 28, bores 32 are most clearly shown in FIG. 2.

Adjacent housings also define in combination, when assembled, spaced apart slots 36.

A plurality of electrically conductive spring rings 40 are disposed in corresponding slots 36. The spring rings 40 may be cut to size from tubing and thus are dimensionally accurate and consistent from ring to ring. The rings may be fabricated from any suitable metal acceptable for implants.

As also shown, a plurality of electrically conductive garter springs 44 are provided with each spring being disposed within a corresponding spring ring 40, each spring ring being aligned with a respective terminal 50 on a rod portion 54 of the implanted lead 12.

As shown in FIG. 2, a setscrew housing 58 may be provided for receiving a setscrew 60 for enabling compacted assembly of the housings 28 between a molded end cap 64.

One or more cables 68 (see FIG. 1) including a plurality of wires 70 are provided with each wire 70 attached to a corresponding spring ring 40 as best illustrated in FIG. 7 through a window 76 formed in each of the housings 28.

Again with reference to FIG. 2, snap fittings 80 may be provided for removably holding adjacent housings 28 to one another, the snap fitting 80 may include overlapping circumferential portions 84.

Alternatively, as best shown in FIGS. 4, 6, and 7, the housings may be assembled in a line through the use of housing holes 90 with pins 92 therethrough.

In order to provide a seal between housings, the housings 28 further define seal grooves 96 and a plurality of washer seals 98 may be disposed therein. Such washer seals 98 may be formed from any suitable material.

Although there has been hereinabove described a specific electrical conductive path for a medical electronics device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An electrical conductive path for a medical electronic device, the conductive path comprising:
    a plurality of stackable molded non-conductive housings, each housing having a bore therethrough alignable with adjacent housing bores, said adjacent housings defining, in combination, spaced apart slots;
    a plurality of electrically conductive spring rings, each ring disposed in a corresponding slot;
    a plurality of electrically conducting garter springs, each spring disposed within a corresponding spring ring;
    snap fittings removably holding the adjacent housings to each other; and
    a cable having a plurality of wires, each wire attached to a corresponding spring ring.

2. The path according to claim 1 wherein each housing includes an alignable hole and the path further comprises pins for aligning the housing holes.

3. The path according to claim 1 wherein the adjacent housing further define, in combination, seal grooves and the path further comprises a plurality of washer seals, each washer seal being disposed in a corresponding seal groove.

4. The path according to claim 3 further comprising snap fittings removably holding adjacent housings to each other.

5. The path according to claim 1 wherein the housing includes windows exposing the spring rings.

6. The path according to claim 5 wherein the wires are attached to the corresponding spring rings within the windows.

7. The path according to claim 1, wherein said snap fittings comprise overlapping circumferential portions of each adjacent housings.

8. An electrical conductive path for a medical electronic device, the conductive path comprising:
- a header;
- a plurality of stackable molded non-conductive housings disposed in said header, each housing having a bore therethrough alignable with adjacent housing bores, said adjacent housings defining, in combination, spaced apart slots;
- a plurality of electrical conductive spring rings, each ring disposed in a corresponding slot;
- a plurality of electrically conducting garter springs, each spring disposed within a corresponding spring ring;
- a cable having a plurality of wires, each wire attached to a corresponding spring ring;
- a lead including a rod receivable by the housing bores, said rod having a plurality of spaced apart electrical terminals corresponding to the spaced apart spring slots;
- snap fittings removably holding the adjacent housings to each other; and
- a latch removably holding the rod in position within the bores with electrical connection between corresponding rod terminals and springs.

9. The path according to claim 8 wherein each housing includes an alignable hole and the path further comprises pins for aligning the housing holes.

10. The path according to claim 8, wherein the adjacent housing further define, in combination, seal grooves and the path further comprises a plurality of washer seals, each washer seal being disposed in a corresponding seal groove.

11. The path according to claim 10 further comprising snap fittings removably holding adjacent housings to each other.

12. The path according to claim 8 wherein the housing includes windows exposing the spring rings.

13. The path according to claim 12 wherein the wires are attached to the corresponding spring rings within the windows.

14. The path according to claim 8 wherein said snap fittings comprise overlapping circumferential portions of each adjacent housings.

* * * * *